US011227681B2

(12) United States Patent
Wilson et al.

(10) Patent No.: US 11,227,681 B2
(45) Date of Patent: Jan. 18, 2022

(54) DEVICE FOR MONITORING THE USE OF BLISTER PACKAGED CONTENTS AT A DISTANCE

(71) Applicant: Intelligent Devices SEZC Inc., Grand Cayman (KY)

(72) Inventors: Allan Wilson, Ottawa (CA); Michael Petersen, Ottawa (CA); Dean Brotzel, Ottawa (CA)

(73) Assignee: Intelligent Devices SEZC Inc., Grand Cayman (KY)

( * ) Notice: Subject to any disclaimer, the term of this patent is extended or adjusted under 35 U.S.C. 154(b) by 0 days.

(21) Appl. No.: 16/359,339

(22) Filed: Mar. 20, 2019

(65) Prior Publication Data

US 2019/0295705 A1    Sep. 26, 2019

(51) Int. Cl.
| | | |
|---|---|---|
| *G16H 20/13* | (2018.01) | |
| *G08B 5/22* | (2006.01) | |
| *G08B 21/24* | (2006.01) | |
| *G10L 25/48* | (2013.01) | |
| *A61J 1/03* | (2006.01) | |
| *G08B 3/02* | (2006.01) | |

(52) U.S. Cl.
CPC .............. *G16H 20/13* (2018.01); *A61J 1/035* (2013.01); *G08B 3/02* (2013.01); *G08B 5/22* (2013.01); *G08B 21/24* (2013.01); *G10L 25/48* (2013.01); *A61J 2200/30* (2013.01)

(58) Field of Classification Search
CPC .......... G16H 20/13; G08B 5/22; G08B 21/24; G08B 3/02; A61J 2200/30; A61J 1/035; G10L 25/48; H04N 11/00; G01H 3/14; H04R 29/00; H04R 3/005; H04S 7/40

USPC .......................................................... 381/56
See application file for complete search history.

(56) References Cited

U.S. PATENT DOCUMENTS

| | | | | |
|---|---|---|---|---|
| 10,025,908 | B1 * | 7/2018 | Orellano ................ | G16H 40/63 |
| 2005/0223826 | A1 * | 10/2005 | Petersen ............... | A61J 7/0481 |
| | | | | 73/865.9 |
| 2010/0094455 | A1 * | 4/2010 | Dehlin ................. | A61J 7/0436 |
| | | | | 700/232 |
| 2015/0363570 | A1 * | 12/2015 | Hanina ................ | A61B 5/1128 |
| | | | | 348/143 |
| 2016/0196560 | A1 * | 7/2016 | Nolan ................... | G06Q 30/01 |
| | | | | 700/94 |
| 2017/0225854 | A1 * | 8/2017 | Brotzel .................. | G16H 20/13 |

\* cited by examiner

*Primary Examiner* — Ahmad F. Matar
*Assistant Examiner* — Sabrina Diaz
(74) *Attorney, Agent, or Firm* — Hodgson Russ LLP

(57) ABSTRACT

There is provided a device for monitoring the use of a blister package, strip package, vial or bottle contents at a distance. A processor is connected to a compact random or quasi-random n-microphone array and is programmed to detect the sound of the content being expelled from a blister cavity, strip package, or a cap being removed from a vial or bottle. A content use data memory associated with the processor stores information relating to the expulsion or removal events. The processor is equipped with statistical means for differentiating the sound of the content being expelled, from the background noise, generating an electrical signal that is analyzed for relevance to content use events by the processor, and storing the resulting use data in memory. The processor may have an adaptive beam focussing algorithm to determine the direction of the source of the sound.

37 Claims, 2 Drawing Sheets

DEVICE FOR MONITORING THE USE OF BLISTER PACKAGED CONTENTS AT A DISTANCE

FIELD OF THE INVENTION

This invention relates to a content use and monitoring system for blister packaged items and vial or bottle packaged items, and more particularly, to a device and content use monitoring system that is suitably used for medication packaging and dispensing but is not limited to medication packaging. Further, the invention does not rely on electronic tags or conductive traces carried on or in the blister package, vial or bottle as described in prior art.

BACKGROUND OF THE INVENTION

Medications are most commonly packaged in vials or bottles; however, blister packaging is widely used in the packaging industry, and is the most rapidly growing packaging method for medication. There is also developing interest in strip packaging of medication.

A limiting factor to the effectiveness of medications is patient compliance (adherence) with the prescription. Medications are required to be taken at specific intervals based on their pharmacokinetics to optimize plasma levels, and deviation from the prescribed interval. Failure to take a dose, or taking extra doses may result in ineffectiveness or adverse effects. It is well documented that patients are only between 50 and 65 percent compliant with medication instructions. The error created by non-compliance interferes with accurate decision-making in both clinical trials of new drugs and in general medical practice.

It is widely acknowledged that it would be useful to researchers and prescribing physicians and pharmacists to have a record of their patients' compliance with medication regimens. This information could then be used to increase the accuracy of drug trial results, and also prevent unnecessary and expensive changes in medication in clinical settings where the lack of a clinical response is actually due to poor compliance.

Devices for monitoring, recording and downloading medication compliance data for vials and blister packages are well known. Allan Wilson, Michael Petersen, Dean Brotzel, Jakob Ehrensvaerd and Stina Grip, amongst others, have described such devices for blister packaged medication, for example U.S. Pat. Nos. 7,113,101, 7,178,417, 6,628,199, 6,244,462, 7,170,409, 6,616,035, 7,616,116 and 7,772,974; PCT applications WO/2009/135283, and WO 2013/159198 A1; Canadian application No. 2353350 and US Publication Nos. 20070278285, 20080191174 and 20080053222.

For blister packaging, such devices broadly comprise sensor detecting/monitoring electronic processors, sensor grids printed with conductive ink, and means of connecting the two.

For vial and bottle packaging such devices comprise a cap with electromechanical or optical switch means to detect cap openings and in-cap electronics to process and store the cap opening data.

Devices relying on opening events are less useful than those relying on blister package expulsion events as they conflate a range of misuse (e.g. not taking a content or taking variable amounts of extra content).

In addition to medication, such devices are suited to monitoring the use of any content the form factor of which is appropriate for blister packaging, bottle or vial dispensing, and strip packaging.

However, all such devices are complicated in that they utilize electromechanical or optical switches (bottles or vials) or a printed grid integrated into the package in close correspondence with the pattern of blister cavities (blister packages and strip packages). Both blister packaging and vial dispensing require on-board electronics to detect and record opening events, and blister packaging requires means of reliably locating the grid in proximity to the blister cavities and means of connecting the grid to the electronics. Strip packaging requires a conductive grid and an electronic reader.

To reduce the complexity added by the printed grid and associated electronics, Michael Petersen and Allan Wilson describe a method for monitoring, recording and downloading medication-dispensing histories for blister packaged medication that eliminates the printed grid (U.S. Pat. No. 7,178,417). This method relies on the piezo-electric effect that generates a signal derived from the pattern of vibrations created when the content is expelled from a blister cavity.

While conceptually simpler and of broader applicability, the piezo-electric method requires on-board electronics with adequate memory to do the calculations required to detect the piezo-electric effect generated signal, and considerable power (battery) to perform the required signal-to-noise (S/N) differentiating calculations.

SUMMARY OF THE INVENTION

In one aspect of the present invention there is provided a medication monitoring system for blister packaged, vial packaged and strip packaged medication and other suitable contents that eliminates the printed grid (blister and strip package) and on-board electronics (blister and vial package) and obviates the need for on-board electronics and power source (battery).

The proposed device uses a centrally-located quasi-random microphone array (for example Google Home® or Amazon Echo®) to detect the sound generated by the expulsion of the content from a cavity of a blister package located in proximity to the array, the sound of a nearby vial cap being opened and/or a content being removed, or the sound of a strip package being torn open. These means can also incorporate the sound of epiglottic closure (swallowing) as a means of confirming content ingestion.

In one aspect of the present invention a quasi-random microphone array is utilized with the microphones mounted on a horizontal plane. The array may be dedicated to the proposed device or borrowed from an existing similar device such as Amazon Echo® or Google Home®. The device is deployed in a room where medication is likely to be removed from a blister package, strip package or vial.

One embodiment involves a processor that receives signals form the microphone array. The processor has analog-to-digital conversion (ADC) capability, a timing device (clock), an optional back up battery, and memories for storing content use data and procedure use data.

The procedure can use data memory that is preprogrammed with statistical means for differentiating the sound signal created by the content being expelled from a blister from the background noise in the room (signal detection program). This may or may not include a brief training session at the time of set-up, as is the case for voice recognition programs.

This means may optionally be augmented by an adaptive beam-focussing algorithm to further increase the discriminability of the S/N ratio by localizing the blister package in the room prior to the S/N analysis.

For bottle and vial packaged medication, the procedure can use data memory that is programmed with similar means for detecting the opening of a vial cap, the removal of a content from a vial, or a combination thereof.

For strip packaged medication, the procedure can use data memory that is programmed with similar means for detecting the tearing open of a strip package, the removal of a content from a package, or a combination thereof.

Each means may be further combined with detection of epiglottic closing to confirm ingestion of the content.

The procedure can use data memory that is further programmed to determine and record the time of detected opening or content expulsion events, the times of which are stored in the content use data memory.

The processor may be equipped with input/output port means for programming the procedure use data memory and downloading the content use data. The processor may optionally be equipped with transceiver means for wirelessly uploading procedure use data, downloading content use data, and communicating with any wirelessly enabled external device.

Several such devices may be linked wirelessly to work together as in monitoring the several rooms of a house, apartment or personal care facility, for medication use events.

The procedure use memory may be programmed to analyze dynamically the content use data for aberrant use patterns. On detecting such a pattern the device may generate feedback about the pattern, and this feedback may be broadcast directly from the device via a speaker or transmitted wirelessly to a wireless-enabled device such as a tablet or smart phone running an app dedicated to displaying the feedback. Feedback might comprise a motivational message to the patient to correct his/her medication taking, or a warning about potentially dangerous dosing that could be transmitted wirelessly to a physician, other health care worker, or family member alerting them to the problem via a smart device running an app, and possibly triggering a medication intervention.

It may be desirable to engineer aspects of the blister package or strip package to optimize the discriminability of content expulsion events from the background noise. This might involve engineering either the blister material or the backing material to produce a unique sound when distorted or torn by a content being expelled from its blister.

For vial caps it may be desirable to engineer aspects of the cap or vial to optimize the discriminability of cap opening from background noise. The strip packaging material could similarly be engineered to optimize signal detection.

It may also be desirable in certain situations for the device to detect and record, either separately or interchangeably, both cap opening events and package expulsion events for patients taking multiple medications.

The proposed device may also be used to detect the opening of "smart" cap devices (e.g.: MEMsCap®; eCap™) by recognizing the sound of their opening sensors (switches) or associated alerting beeps or other sounds.

In one aspect of the present invention there is provided a monitoring device comprising: a microphone array; a processor connected to the microphone array; said processor configured to detect a sound of a content being expelled from a blister cavity or strip package, or a cap being removed from a vial or bottle; said processor having statistical means for differentiating the sound of the content being expelled from the blister cavity or strip package or the cap opening, from background noise, said processor analyzing the sound of the content being expelled from the blister cavity or strip package or the cap opening for relevance to content use events and predetermined procedure data.

In a further aspect of the present invention there is provided a monitoring device further comprising a memory associated with said processor to store content use data relating to the content being expelled from a blister cavity or strip package, or a cap being removed from a vial or bottle.

In a further aspect of the present invention there is provided a monitoring device wherein said processor uses an adaptive beam-focussing algorithm to determine direction of the sound of the content being expelled from a blister cavity, strip package or vial cap being opened, thereby increasing sensitivity of statistical signal to noise ratio analysis.

In a further aspect of the present invention there is provided a monitoring device further comprising a power source connected to said processor, an internal clock and an analog-to-digital converter.

In a further aspect of the present invention there is provided a monitoring device, wherein the processor records a time of detection of the sound, and the content use data includes the time.

In a further aspect of the present invention there is provided a monitoring device further comprising an output port for outputting the content use data to an external device. The procedure data memory may be a programmable memory allowing a monitor to program predetermined procedure data.

In a further aspect of the present invention there is provided a monitoring device further comprising a transmitter for transmitting the content use data to an external device. The transmitter may be a wireless transmitter capable of wirelessly communicating with the external device.

In a further aspect of the present invention there is provided a monitoring device, further comprising a warning generator for generating a warning signal when the content use data violates the predetermined procedure data.

In a further aspect of the present invention there is provided a monitoring device, further comprising a transmitter for sending the content use data to an external device; a receiver for receiving a warning signal from the external device; and a warning device for providing a warning in response to the warning signal.

In a further aspect of the present invention there is provided a monitoring device, wherein the processor analyzes, summarizes and updates the cumulative content use data on an ongoing basis. The summarized cumulative content use data may be readable by an external device. The summarized cumulative use data may be configured to be displayed to inform and motivate a patient to increase compliance.

In another aspect of the present invention there is provided a monitoring system for remotely monitoring use of contents of a blister package having at least one sealable receptacle for accommodating the contents, use of contents of a strip package having at least one sealable package for accommodating the contents or an opening of a vial or bottle cap containing the contents, the system comprising: a microphone array configured to detect a sound of one of the contents being expelled from a blister, sound of one of the contents being expelled from the strip package or sound of the cap being opened; and a processor for detecting and analyzing signals from the array, said processor being configured to differentiate the sound of such opening events from background noise and generate content use data when said signals are detected, wherein the processor could have a use data memory for storing the content use data.

In a further aspect of the present invention there is provided a monitoring device, further comprising a transmitter for transmitting the content use data to an external device. The transmitter may be a wireless transmitter capable of wirelessly communicating with the external device.

In a further aspect of the present invention there is provided a monitoring device, wherein the processor has a procedure data memory for storing predetermined procedure data regarding how to use the blister package, strip packaged or vial contents. The processor may be configured to analyze the content use data as a function of the procedure data, and generate a warning signal for display either on the monitoring device, the blister package or a remote device. The processor may be configured to analyze the content use data as a function of the procedure data and generate summary display data for display on a remote device for the purpose of giving feedback to a patient and motivating increased compliance. The processor could have a transmitter and a receiver for communicating with an external device to program the procedure data memory.

In a further aspect of the present invention there is provided a monitoring device, wherein the blister package is configured to generate a unique sound when one of the contents is expelled from the sealable receptacle. The blister package could have a foil backing that is configured to generate a unique sound when one of the contents is expelled from the sealable receptacle.

In a further aspect of the present invention there is provided a monitoring device, wherein the cap is configured to generate a unique sound on opening from the bottle or vial.

In a further aspect of the present invention there is provided a monitoring device, wherein the vial or bottle is configured to generate a unique sound upon opening of the cap from the vial or bottle.

In a further aspect of the present invention there is provided a monitoring device, wherein the strip package material is configured to generate a unique sound on opening.

In a further aspect of the present invention there is provided a monitoring device, further comprising a warning device for providing a warning in response to the warning signal. The warning device may be on the vial, vial cap or blister package. A transmitter could be provided for transmitting the warning signal to an external device, wherein the warning device is provided in the external device. Furthermore, a receiver could be provided for allowing the procedure data memory to be programmed from a remote wireless device.

In a further aspect of the present invention there is provided a monitoring device, wherein the processor is configured to recognize unique sounds generated upon opening of the blister package, strip package, vial, bottle or cap.

BRIEF DESCRIPTION OF THE DRAWINGS

The device will be further understood from the following description with reference to the drawings in which.

DETAILED DESCRIPTION OF THE PREFERRED EMBODIMENTS

Figure 1:
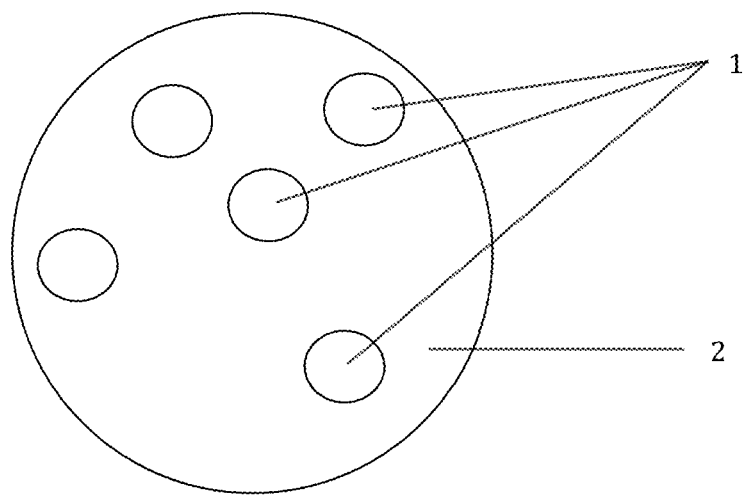
FIG. 1 is a plan view of the device.

FIG. 1 depicts an adherence-monitoring device in accordance with an embodiment of the present invention. The device comprises an inventory monitoring system that can either be free standing or added to an existing n-microphone array 1 that is part of a device such as Google Home® or Amazon Echo® the microphones of which are distributed quasi-randomly or randomly on a horizontal plane 2 at the top of the device.

FIG. 1 refers to a content use monitoring device in accordance with an embodiment of the present invention. The device comprises a random or quasi-random microphone array 1 of n microphones located on a horizontal plane centrally located in a room where blister packaged contents are anticipated to be expelled from their cavities or caps removed from their vials. Alternatively the microphone array 1 might form part of a freestanding device such as Amazon Echo® or Google Home®.

Figure 2:
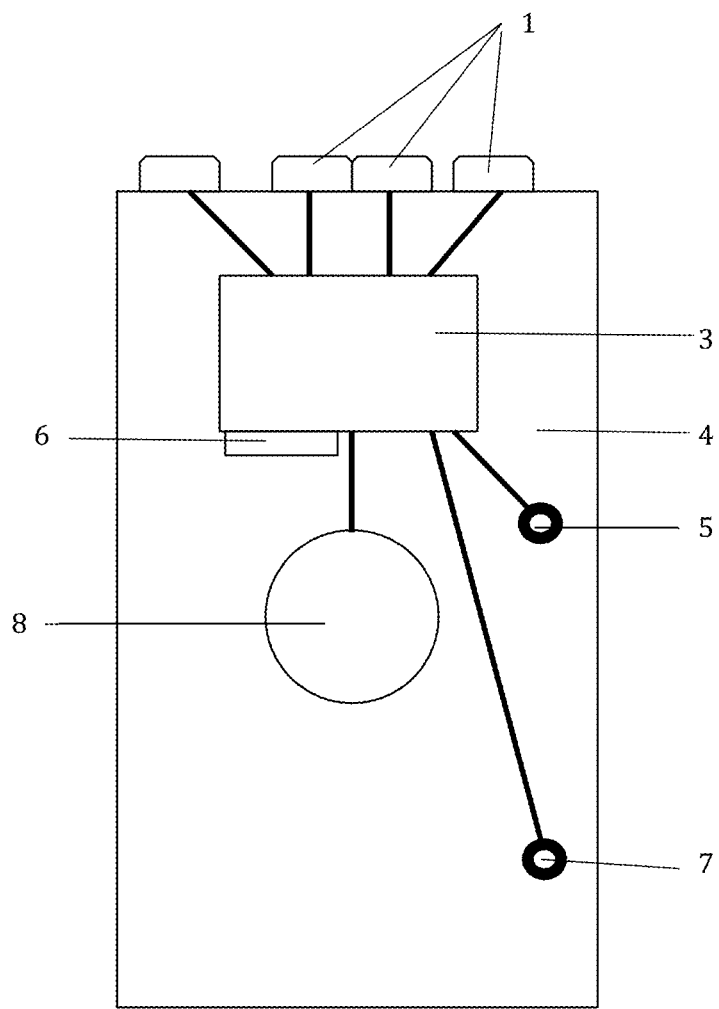
FIG. 2 is an elevation view of the device.

As shown in FIG. 2, in one aspect each microphone in the microphone array 1 is individually connected to a processor 3 located within the body 4 of the device. The processor 3 may have an ADC, clock, internal or external volatile or non-volatile use data and procedure data memories, I/O port 5, back-up battery 6 and input power source 7. The processor may be further connected to a transceiver 8 capable of two-way wireless communication with wirelessly enabled external devices. The processor 3 receives input signals from the individual microphones. In one aspect a minimum of two memories are dedicated to procedure use data and content use data.

The device may also be equipped with an input/output port 5 to permit uploading instructions to the procedure use data memory and downloading content use data from the device. The device may optionally be equipped with a transceiver 8 to facilitate uploading instructions and downloading content use data or otherwise communicating wirelessly with any wireless external device or system.

In use, the device may be situated in a room where the content of a blister package may be expelled or a vial cap removed. The procedure use data memory is programmed with an algorithm to detect the sound using adaptive statistical signal-to-noise (S/N) differentiating analysis. In some cases, the program will benefit from a brief training session; in others the S/N profile will already have been determined for that type of blister package and content or vial cap and programmed into the procedure use data memory. To facilitate the process of differentiating signal from noise, the procedure use data memory may also include a fixed or adaptive beam-focussing algorithm to localize the sound in the room and increase the accuracy of the statistical S/N analysis.

When the S/N analysis is consistent with a content expulsion or opening event, the processor 3 determines the time and enters the event details into the content use data memory. The content use data may be stored in the processor 3 for retrieval at a later time or may be downloaded via the i/o port 5, or transceiver 8 wirelessly, or subjected to further analysis by the processor 3 as, for example, to generate a warning of aberrant dose taking based on preprogrammed criteria, the warning being transmitted to the wireless external device (e.g., smart phone) of the patient or caregiver (e.g. health care worker or family member). Content use data can typically be uploaded from the device to a cloud-based server for further analysis and action.

It may be desirable to monitor the medication-taking behaviour of several patients in the same location and with the same medication monitoring device (e.g. family members, patients in a self-care facility). The proposed medication monitoring device may optionally be equipped with means of differentiating multiple users. Such means might include sensor fusion including but not limited to optical facial recognition means, LIDAR means, and CMOS radar means the data from which sensors are analyzed by statistical signal/noise differentiating software optionally augmented by adaptive two-dimensional beam focussing algorithms to increase directional precision or adaptive three-dimensional beam focussing algorithms to aid in identifying the patient by height.

In one example, it may be desirable to engineer aspects of the blister package or strip package to optimize the discriminability of content expulsion events from the background noise. This might involve engineering either the blister material or the backing material to produce a unique sound when distorted or torn by a content being expelled from its blister. Similarly, the cap could be engineered to provide a unique sound on opening, or the vial or bottle could be engineered to provide a unique sound when the cap is removed. It will be appreciated that there are various different ways to configure the blister package, vial, cap or strip packaging to make a unique sound, such as through use of special materials-engineered plastics, foils, etc that could be selected and designed to generate a distinctive sound profile when tablets are expelled. The sound profile can be stored in the processor.

In another aspect of the present invention, the monitoring system could include a warning device for providing a warning in response to the warning signal. The warning device could be on the vial, vial cap or blister package or in an external device. A transmitter could be used to transmit the warning signal to the external device and the warning device could be provided in the external device. For example, a speaker or similar audio generator could be located on the microphone array unit, such as an Echo unit, or on the blister package, bottle, cap, mobile device or other remote terminal or external device.

It will be appreciated by one skilled in the art that variants can exist in the above-described arrangements and applications. The scope of the claims should not be limited by the preferred embodiments set forth in the examples, but should be given the broadest interpretation consistent with the description as a whole.

What is claimed is:

1. A monitoring device for remotely monitoring and tracking usage of contents from a medication package comprising:
    a microphone array;
    a processor connected to the microphone array;
    a memory associated with said processor to store content use data relating to the content being expelled from the medication package; and
    a sensor for differentiating a user, wherein the sensor uses sensor fusion which brings together inputs selected from the group consisting of optical facial recognition sensors, LIDAR, CMOS radar and combinations thereof;
    said processor configured to detect a sound of a content being expelled from the medication package;
    said processor having statistical means for differentiating the sound of the content being expelled from the medication package from background noise;
    said processor analyzing the sound of the content being expelled from the medication package for relevance to predetermined procedure data;
    wherein the predetermined procedure data includes instructions for use of the contents of the medication package;
    wherein the processor includes statements and instructions to analyze dynamically the content use data for aberrant use patterns;
    wherein upon detecting an aberrant use pattern the processor generates feedback about the pattern;
    wherein the feedback is broadcast to the user; and
    wherein data from the sensor fusion is analyzed by the processor using statistical signal/noise differentiating software and augmented by adaptive two-dimensional beam focussing algorithms to increase directional precision or adaptive three-dimensional beam focussing algorithms to aid in identifying the user by height.

2. The monitoring device of claim 1 wherein said processor uses an adaptive beam-focussing algorithm to determine direction of the sound of the content being expelled from a blister cavity, strip package or vial cap being opened, thereby increasing sensitivity of statistical signal to noise ratio analysis.

3. The monitoring device of claim 1 further comprising a power source connected to said processor, an internal clock and an analog-to-digital converter.

4. The monitoring device of claim 1, wherein the processor records a time of detection of the sound, and the content use data includes the time.

5. The monitoring device of claim 1, further comprising an input/output port for outputting the content use data to an external device and receiving updates to the procedure data.

6. The monitoring device of claim 1, further comprising a transmitter for transmitting the content use data to an external device.

7. The monitoring device of claim 6, wherein the transmitter is a wireless transmitter capable of wirelessly communicating with the external device.

8. The monitoring device of claim 1, further comprising a warning generator for generating a warning signal when the content use data violates the predetermined procedure data.

9. The monitoring device of claim 1, further comprising a transmitter for sending the content use data to an external device; a receiver for receiving a warning signal from the external device; and a warning device for providing a warning in response to the warning signal.

10. The monitoring device of claim 1, wherein the processor analyzes, summarizes and updates the content use data on an ongoing basis.

11. The monitoring device of claim 10, wherein the summarized cumulative content use data are readable by an external device.

12. The monitoring device in claim 10, wherein the summarized cumulative use data are configured to be displayed to inform and motivate a patient to increase compliance.

13. The monitoring device of claim 1 wherein said processor is further configured to detect a sound of an epiglottic closing to confirm ingestion of the content.

14. The monitoring device of claim 1 wherein the feedback is provided via a speaker or transmitted wirelessly to a wireless-enabled device or provided on a display.

15. The monitoring device of claim 14 wherein the feedback comprises a motivational message for the user to correct his/her medication taking, or the feedback comprises a warning about potentially dangerous dosing for a physician, other health care worker, or family member.

16. The device of claim 1 wherein the processor is further configured to include an algorithm to detect the sound using adaptive statistical signal-to-noise (S/N) differentiating analysis.

17. The device of claim 1 wherein the processor is further configured to include a training session for learning to differentiate the sound of the content being expelled from the medication package from background noise.

18. A monitoring system for remotely monitoring use of contents of a blister package having at least one sealable receptacle for accommodating the contents, use of contents of a strip package having at least one sealable package for accommodating the contents or an opening of a vial or bottle cap containing the contents, the system comprising:
 a microphone array configured to detect a sound of one of the contents being expelled from a blister, sound of one of the contents being expelled from the strip package or sound of the cap being opened;
 a processor for detecting signals from the array, said processor being configured to differentiate the sound of such opening events from background noise and generate content use data when said signals are detected;
 a sensor for differentiating a user, wherein the sensor uses sensor fusion which brings together inputs selected from the group consisting of optical facial recognition sensors, LIDAR, CMOS radar and combinations thereof; and
 a transmitter for uploading content use data to an external device for analysis;
 wherein the processor or external device has a procedure data memory for storing predetermined procedure data regarding how to use the blister package, strip package or vial contents;
 wherein the processor or external device includes statements and instructions to analyze dynamically the content use data for aberrant use patterns;
 wherein upon detecting an aberrant use pattern the processor or external device generates feedback about the pattern;
 wherein the feedback is broadcast to the user; and
 wherein data from the sensor fusion is analyzed by the external device or processor using statistical signal/noise differentiating software and augmented by adaptive two-dimensional beam focussing algorithms to increase directional precision or adaptive three-dimensional beam focussing algorithms to aid in identifying the user by height.

19. The monitoring system of claim 18, wherein the transmitter is a wireless transmitter capable of wirelessly communicating with the external device.

20. The monitoring system in claim 18, wherein the processor is configured to analyze the content use data as a function of the procedure data, and generate a warning signal.

21. The monitoring system of claim 20 further comprising a warning device for providing a warning in response to the warning signal.

22. The monitoring system of claim 21, wherein the warning device is on the vial, vial cap or blister package.

23. The monitoring system of claim 21, wherein the transmitter transmits the warning signal to the external device, and the warning device is provided in the external device.

24. The monitoring system of claim 18, wherein the processor is configured to analyze the content use data as a function of the procedure data and generate summary display data for display on a remote device.

25. The monitoring system of claim 18, further comprising a receiver, wherein the transmitter and the receiver communicate with the external device to program the procedure data memory.

26. The monitoring system of claim 18, wherein the blister package is configured to generate a unique sound when one of the contents is expelled from the sealable receptacle.

27. The monitoring system of claim 26, wherein the blister package has a foil backing that is configured to generate the unique sound when one of the contents is expelled from the sealable receptacle.

28. The monitoring system of claim 18, wherein the cap is configured to generate a unique sound on opening from the bottle or vial.

29. The monitoring system of claim 18, wherein the vial or bottle is configured to generate a unique sound upon opening of the cap from the vial or bottle.

30. The monitoring system of claim 18, wherein the strip package material is configured to generate a unique sound on opening.

31. The monitoring system of claim 18, wherein the processor is configured to recognize unique sounds generated upon opening of the blister package, strip package, vial, bottle or cap.

32. The monitoring system of claim 18 wherein said processor is further configured to detect a sound of an epiglottic closing to confirm ingestion of the content.

33. The system of claim 18 wherein the processor is further configured to include an algorithm to detect the sound using adaptive statistical signal-to-noise (S/N) differentiating analysis.

34. The system of claim 18 wherein the processor is further configured to include a training session for learning to differentiate the sound of the opening event from background noise.

35. A monitoring device for remotely monitoring and tracking usage of contents from a medication package comprising:
 a microphone array;
 a processor connected to the microphone array;
 a memory associated with said processor to store content use data relating to the content being expelled from the medication package;
 a sensor for differentiating a user, wherein the sensor uses sensor fusion which brings together inputs selected from the group consisting of optical facial recognition sensors, LIDAR, CMOS radar and combinations thereof; and
 a transceiver for uploading the content use data to an external device for analysis to determine relevance to predetermined procedure data which includes instructions for use of the contents of the medication package, and to analyze dynamically the content use data for aberrant use patterns;
 said processor configured to detect a sound of a content being expelled from the medication package;

said processor having statistical means for differentiating the sound of the content being expelled from the medication package from background noise;

wherein upon detecting an aberrant use pattern the transceiver receives feedback about the pattern form the external device;

wherein the feedback is broadcast to the user;

wherein data from the sensor fusion is analyzed by the processor using statistical signal/noise differentiating software and augmented by adaptive two-dimensional beam focussing algorithms to increase directional precision or adaptive three-dimensional beam focussing algorithms to aid in identifying the user by height.

36. The device of claim 35 wherein the processor is further configured to include an algorithm to detect the sound using adaptive statistical signal-to-noise (S/N) differentiating analysis.

37. The device of claim 35 wherein the processor is further configured to include a training session for learning to differentiate the sound of the content being expelled from the medication package from background noise.

\* \* \* \* \*

UNITED STATES PATENT AND TRADEMARK OFFICE
CERTIFICATE OF CORRECTION

PATENT NO. : 11,227,681 B2
APPLICATION NO. : 16/359339
DATED : January 18, 2022
INVENTOR(S) : Wilson et al.

It is certified that error appears in the above-identified patent and that said Letters Patent is hereby corrected as shown below:

On the Title Page

Item (30) should read:
--(30) Foreign Application Priority Data
Mar. 20, 2018 (CA) ........................ 2998627--

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*